United States Patent [19]

Loefqvist

[11] Patent Number: 4,566,436
[45] Date of Patent: Jan. 28, 1986

[54] METHOD FOR APPLYING AND/OR KEEPING AN ISCHAEMIC AREA DURING SURGERY ON THE LIMBS

[75] Inventor: Johan Loefqvist, Finspång, Sweden
[73] Assignee: HB Varix, Finspång, Sweden
[21] Appl. No.: 499,757
[22] PCT Filed: Sep. 30, 1982
[86] PCT No.: PCT/SE82/00303
   § 371 Date: May 24, 1983
   § 102(e) Date: May 24, 1983
[87] PCT Pub. No.: WO83/01192
   PCT Pub. Date: Apr. 14, 1983

[30] Foreign Application Priority Data

Oct. 2, 1981 [SE] Sweden .............................. 8105819

[51] Int. Cl.$^4$ .............................................. A61B 17/12
[52] U.S. Cl. .................................. 128/1 R; 128/327
[58] Field of Search ...................... 128/57, 58, 60, 61, 128/67, 24.3, 325, 327, 686, 1 R

[56] References Cited

U.S. PATENT DOCUMENTS 3,756,239  9/1973  Smythe ............................ 128/327
4,066,084  1/1978  Tillander .......................... 128/327
4,228,792  10/1980 Rhys-Davies ................. 128/327 X
4,269,177  5/1981  Clark ................................ 128/57

Primary Examiner—Michael H. Thaler
Attorney, Agent, or Firm—Flynn, Thiel, Boutell & Tanis

[57] ABSTRACT

This invention relates to a device for applying and/or keeping an ischaemic area during surgery on the limbs. The conventional technique is to tightly wrap the limb in question with rubber strips called an Esmarch bandage whereby ischaemia is achieved. This is maintained by means of a conventional tourniquet which is fastened around a thigh or upper arm respectively. During surgery on a ischaemic area it sometimes happens that the surgeon needs to reach the area under the cuff.

With a device according to this invention, a so-called roll-on cuff, this disadvantage amongst others is eliminated as the roll-on cuff can be moved during the operation without jeopardizing the ischaemic area. The roll-on cuff consists of an elastic tube (1; 3, 4), preferably of rubber, where the inner cavity is filled with a gas, preferably air, or a liquid. Furthermore the walls of the inner cavity of the tubes are filled with a lubricant (2), preferably silicone oil, to facilitate rolling on and off. The roll-on cuff is locked on a cone-shaped part of a limb by means of another cuff (4) on which the cuff (3), placed on the bigger diameter of the limb, is allowed to roll onto until a state of equilibrium is reached. The friction between the two cuffs is, due to the nature of the material, enough to keep the cuffs (3, 4) in place.

1 Claim, 6 Drawing Figures

METHOD FOR APPLYING AND/OR KEEPING AN ISCHAEMIC AREA DURING SURGERY ON THE LIMBS

FIELD OF THE INVENTION

This invention relates to a device for applying and/or keeping an ischaemic area during surgery on the limbs.

BACKGROUND OF THE INVENTION

Operating on an ischaemic area is an established method during surgery on the limbs. Virtually all kinds of surgery on the knees, hands and ankles are carried out in an ischaemic area. The advantage with an ischaemic area is that no disturbing bleedings occur and that the surgeon therefore can better see the structures he is interested in. Thus the operation can be carried out quicker and with a greater anatomical certainty.

At the moment an ischaemic area is applied as follows; the limb is wrapped with so-called Esmarch's bandages. Said bandages are made of 1 dm wide, 5 m long and 1-3 mm thick rubber strips. The limb is hereby emptied of blood. The limb is wrapped tightly beginning from its end, i.e. the hand or the foot, and continuing towards the trunk to a point on the upper arm or the thigh, respectively, where a pressure cuff is applied. The pressure cuff is pumped up to a pressure of 50-100 mm Hg above the patient's blood pressure. The thicker the limb is, the higher the pressure needed to achieve ischaemia, if a cuff with a certain width is used. As the blood pressure can vary during the operation, an arm cuff is usually pumped up to 250-300 mm Hg and a leg cuff to 300-500 mm Hg if usual cuffs are used, whereby one is usually sure of keeping the operating area ischaemic. To avoid injuries caused by pressure, as low a pressure as possible is desirable. It is possible to operate in an ischaemic area for 1½-2 hours without any clinical damage occurring. It has been shown that the first injuries to occur in an ischaemic area are pressure injuries on, above all, the nerves which pass under the cuff. The most obvious damages can be found in the tissue under the edges of the cuff. Here the pressure stresses are combined with a mechanical deformation of the tissues based on the so-called shear stresses, which are greatest under the edges of the cuff. It is therefore, desirable to keep as low a highest pressure as possible and to achieve a step-by-step reduction of the pressure towards the edges of the cuff. This can be achieved with a wide contact surface and two or more cuffs.

The problems that are connected with applying and keeping an ischaemic area by means of conventional techniques are:

It is troublesome, laborious and hazardous to empty blood from the limb with the Esmarch bandages. It has happened that front teeth have been knocked out when the elastic strips have burst.

The pressure cuffs and the control mechanism are expensive and not completely reliable.

Clinics that do not have sterile Esmarch bandages and pressure cuffs cannot apply a sterile ischaemic area. The time it takes to achieve an ischaemic area is then prolonged by the time of washing and preparation of the limb in question.

The cuff cannot be moved on the limb during an operation while maintaining the ischaemic area.

SUMMARY OF THE INVENTION

An object of the present invention is to achieve a device of the above type with which the above problems are eliminated, and this is achieved by the fact that the device includes one or more cuffs in the shape of elastic tubes which are filled with a liquid, a gas or another media and which it is possible to roll on and off the extremity.

Additional advantages with the device according to the invention are:

Ischaemia is achieved when the cuff is rolled on, which is quicker, easier and safer than binding up with rubber bandages.

The roll-on cuffs are possible to sterilize, which permits the ischaemic area to be applied just before an operation is started. This shortens the time of ischaemia equivalent to the time of preoperative washing and preparation. Furthermore, the risk that a patient will be lying waiting for his/her surgeon with an applied ischaemic area decreases, as said area quickly and neatly can be applied by the surgeon without considerable delay.

The roll-on cuffs can be moved while operating without the ischaemia being jeopardized. This makes it possible to prolong the incision under the cuff. When operating on varicose veins in an ischaemic area it will be possible to reach the varicosities under the cuff. During longer operations local pressure injuries, under the cuff, can be decreased as the cuff can be moved to a new position.

A more certain pressure control is achieved. The elasticity of the cuffs, which preferably are made of rubber, is dimensioned so that too high a pressure cannot occur at the diameters that are of interest on limbs. Only in extreme and exceptional cases will the roll-on cuffs be too small. The pressure under the cuffs can be read in a diagram showing the perimeter of the limb in relation to the pressure under the cuffs by plotting the perimeter in question.

The equipment is simpler than conventional equipment. No pressurized air is required at the operation and fewer troublesome hoses are needed around the operating table.

A more propitious allocation of the pressure is achieved. A wide contact surface and step-by-step reduction of the pressure results in that the local pressure on the tissue being kept lower as compared with conventional techniques. The pressure is highest within the area where the cuffs are over-lapping (verified with pressure measurements and X-ray, which demonstrates the deformation of the tissues). The pressure decreases gradually in the proximal and distal directions. The more rounded ends of the deformation of the tissues, compared with a conventional cuff, can be assumed to decrease the risk of damages because of the so-called edge effect under the cuff, which is the cause of a dislocation of tissue from compressed to non-compressed areas.

BRIEF DESCRIPTION OF THE DRAWINGS

In the following description the invention will be explained further referring to the enclosed drawing, where.

DETAILED DESCRIPTION

Figure 1A:
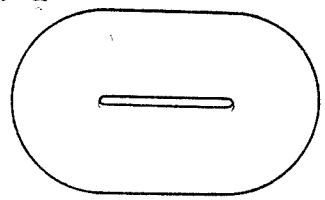
FIG. 1a shows one example of a roll-on cuff according to the invention.
Figure 1B:
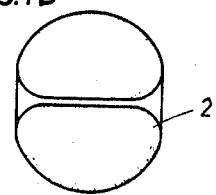
FIG. 1b shows the roll-on cuff according to FIG. 1a as a cross-section. The FIGS. 2a and 2b illustrate how two roll-on cuffs according to the invention are used to achieve an ischaemic area on a leg.
Figure 3:
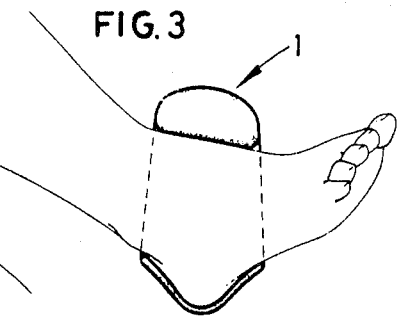
FIG. 3 shows a cross-section of a roll-on cuff in a moment when it is rolled over a foot.

The device according to the invention includes an elastic tube 1 with an inner diameter which is chosen with consideration to the limb for which the tube is intended. The tube is filled with a liquid, a gas or another media and has the shape shown in FIG. 1a. The inner surface of the tube 1 is coated with a lubricant 2, see FIG. 1b, e.g. silicon, oil, glycerine, talc or powder, to reduce friction while rolling the tube on and off the limb. This is because parts of the inner surface of the tube get in contact with each other, see FIG. 3.

Figure 2A:
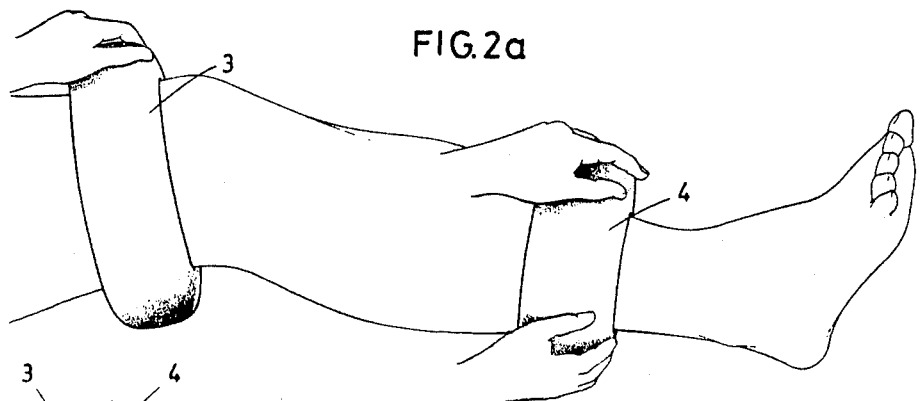
FIG. 2c shows a cross-section of the cuffs in FIG.
Figure 2B:
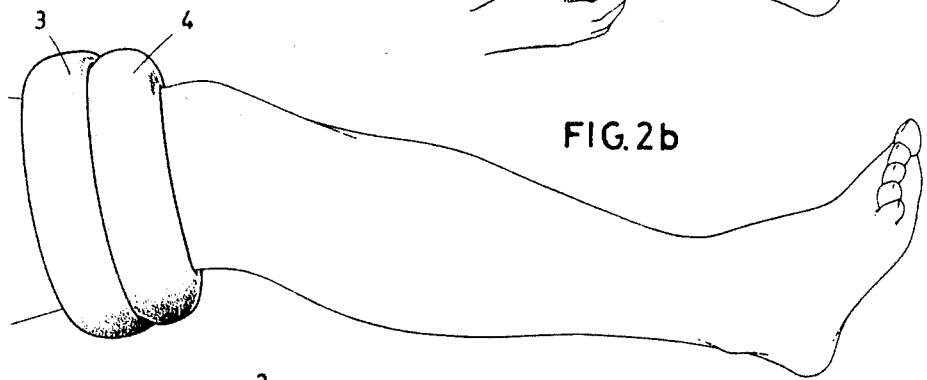
Figure 2C:
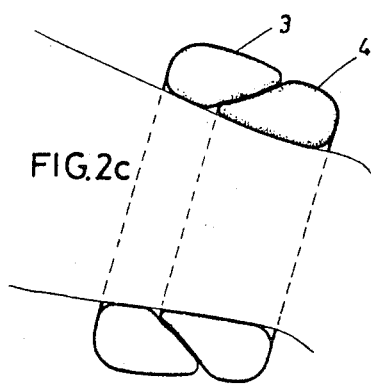

FIG. 2a shows how a proximal roll-on cuff 3 has just been rolled onto a leg and manually is kept in place while a distal cuff 4 is rolled on and in FIG. 2b the proximal cuff 3 has been rolled up on top of the distal roll-on cuff 4, whereby the cuffs effectively interlock. This shows clearly in FIG. 2c which is a sagital cross-section of FIG. 2b. Cuff 4 locks cuff 3 in a wedge-like fashion and the friction between the cuffs 3, 4 and the skin is enough to lock the cuffs against movement along a cone-shaped part of the limb.

The embodiments of the invention in which an exclusive property or privilege is claimed are defined as follows:

1. A method of producing an ischaemic region in a limb during surgery, comprising the steps of: rolling onto the limb a proximal elastic annular tube which is filled with a fluid; thereafter rolling onto the limb a distal elastic annular tube which is filled with a fluid; and thereafter rolling said proximal tube partly onto a portion of said distal tube until a position of equilibrium therebetween is reached in which said tubes are positionally locked against movement along the limb.

* * * * *